United States Patent
Lattime et al.

(10) Patent No.: US 6,177,076 B1
(45) Date of Patent: Jan. 23, 2001

(54) METHOD OF TREATING BLADDER CANCER WITH WILD TYPE VACCINIA VIRUS

(75) Inventors: Edmund C. Lattime, Princeton, NJ (US); Michael J. Mastrangelo, Jenkintown, PA (US)

(73) Assignee: Thomas Jefferson University, Philadelphia, PA (US)

(*) Notice: Under 35 U.S.C. 154(b), the term of this patent shall be extended for 0 days.

(21) Appl. No.: 09/206,425

(22) Filed: Dec. 7, 1998

Related U.S. Application Data

(60) Provisional application No. 60/067,983, filed on Dec. 9, 1997.

(51) Int. Cl.[7] .............................. A01N 63/00; A61K 35/76
(52) U.S. Cl. ....................................... 424/93.6; 424/232.1
(58) Field of Search ................................ 424/93.6, 232.1

(56) References Cited

FOREIGN PATENT DOCUMENTS

WO/95/31105    11/1995   (WO) .

OTHER PUBLICATIONS

Lattime et al. "Strategies for the Use of Recombinant Vaccinia Virus Vectors for the Gene Therapy of Transitional Cell Carcinoma of the Bladder", 6th Annual Fall Symposium of the Society for Basic Urologic Research, Asilomar Conference Center, Pacific Grove, CA (Dec. 12–15, 1996).

L.G. Gomella, et al., "Phase I Study of Intravesical Vaccinia Virus As A Vector For Gene Therapy of Bladder Cancer", *Journal of Urology*, Apr. 13, 1997, vol. 4, Supplement, p. 51, Abstract 194.

S.S. Lee, et al., "Intravesical Gene Therapy: In Vivo Gene Transfer Using Recombinant Vaccinia Virus Vectors", *Cancer Research*, Jul. 1994, vol. 54 pp. 3325–3328.

Edmund C. Lattime, et al., "In Situ Cytokine Gene Transfection Using Vaccinia Virus Vectors", *Seminars in Onclogy*, vol. 23, No. 1 (Feb.), 1996: pp. 88–100.

S.S. Lee et al., "Intravesical gene therapy: Vaccinia virus recombinants transfect murine bladder tumors and urothelium" Proceedings of the American Association for Cancer Research, vol. 34, Mar. 1993, p. 337, Abstr #2005.

L.G. Gomella et al., "Phase I study of intravesical vaccinia virus as a vector for gene therapy of bladder cancer", Proceedings of the American Association for Cancer Research, vol. 38, Mar. 1997, p. 9, Abstr #61.

Dialog Abstract 08915850 of Moss et al., Adv. Exp. Med. Biol. 397:7–13 (1996).

*Primary Examiner*—Donna Wortman
(74) *Attorney, Agent, or Firm*—Seidel, Gonda, Lavorgna & Monaco, PC

(57) ABSTRACT

Methods of treating bladder cancer in a patient by administration of wildtype vaccinia virus are provided.

7 Claims, No Drawings

METHOD OF TREATING BLADDER CANCER WITH WILD TYPE VACCINIA VIRUS

CROSS-REFERENCE TO RELATED APPLICATION

This application claims priority from provisional application Ser. No. 60/067,983, filed Dec. 9, 1997.

REFERENCE TO GOVERNMENT GRANT

This invention was made in the course of research sponsored by the National Institutes of Health grant R21 CA-74543. The U.S. Government may have certain rights in this invention.

BACKGROUND OF THE INVENTION

The standard care for patients with superficial bladder cancer is transurethral resection of the bladder tumor followed by six weeks of intravesical administration of the mycobacterium Bacillus Calmette-Guerin (BCG). This approach not only increases the surgical cure rate but also prolongs the time to recurrence in patients not cured by the surgery. It is believed that the superficial cystitis caused by BCG treatment results in tumor cell death as a bystander effect. However, relapses following this treatment are proving to be more common. Eventually, a significant population of superficial bladder cancer patients will have recurrence of BCG-resistant disease. Currently, there is no good treatment for this group of patients. Accordingly, a more effective treatment is needed for bladder cancer, particularly for superficial cancer and BCG-refractory superficial bladder cancer.

SUMMARY OF THE INVENTION

An object of the present invention is to provide a method of treating patients having bladder cancer which comprises intravesically administering wild type vaccinia virus to the bladder of the patients.

It is a further object of the invention to provide a method of treating patients having superficial bladder cancer, and BCG-refractory superficial bladder cancer in particular, comprising intravesically administering wild type vaccinia virus to the bladder of the patients.

DETAILED DESCRIPTION OF THE INVENTION

Vaccinia virus, a double stranded DNA poxvirus, has been well characterized since its successful use as a live vaccine to prevent smallpox. It has now been found that wild-type vaccinia virus administered intravesically to patients suffering from bladder cancer produces inflammation of the mucosal and submucosal lining of the bladder. The vaccinia virus infects cells lining the bladder including tumor cells thereby leading to their death. Accordingly, the present invention relates to methods of treating patients having bladder cancer which comprises administering to the patient a wild-type vaccinia virus. The method of the present invention is believed to be especially useful in treating patients suffering from superficial bladder cancer.

Wildtype vaccinia virus used in the present invention is prepared in accordance with methods well known to those of skill in the art. The virus is administered in several escalating doses. In one embodiment of this method, the patient is treated with multiple administrations of vaccinia virus intravesically to the bladder. Alternatively, the patient is first vaccinated, preferably via intradermal administration, with the wildtype vaccinia virus. This vaccination is then followed several days later by multiple intravesical administrations of the vaccinia virus directly to the bladder.

For example, the patient may be vaccinated with wild type vaccinia virus on day zero, followed by intravesical administration of vaccinia on days 4, 8 and 11. Each instillation may consist of from about $10^6$ to about $10^8$ vaccinia pock forming units (PFU); lower or higher amounts are also contemplated. For intravesical administration, the virus may be placed in a normal saline solution suitable for intravenous use (without antimicrobials) and deposited in the bladder via urethral catheter.

Superficial bladder cancer is currently treated by transurethral resection of the bladder tumor, followed by intravesical administration of BCG. Vaccinia virus administration according to the present invention is believed particularly useful for treatment of BCG-refractory patients, that is, patients whose bladder cancer is no longer substantially responsive to treatment with BCG.

The ability of vaccinia virus to infect cancer cells was demonstrated in bladder tumor cells. In these experiments, a panel of cell lines including the murine bladder tumors MBT2 and MB49 as well as the human bladder tumor T24 cell line derived from patients were examined for their ability to be infected with a vaccinia virus. Cell lines were exposed in vitro to vaccinia virus recombinants containing marker genes for influenza hemagglutinin and nuclear antigen. After 4.5 hours in culture, the cells were fixed and stained immunohistochemically for the two antigens. All cell lines showed significant levels of staining demonstrating the efficient infection of all bladder tumor cell lines tested.

Experiments were then performed to determine whether the vaccinia virus infects tumor cells and/or normal mucosal cells in vivo. Recombinant vaccinia viruses containing the influenza hemagglutinin and nuclear protein marker genes ($10^7$ PFU) were instilled via urethral catheters into the bladder of C57BL/6 mice bearing the MB49 tumor. After 8 hours, the mice were euthanized, and their bladders were removed, sectioned, and stained for the two antigens using immunohistochemical techniques. Upon microscopic examination, normal bladder mucosa showed evidence of virally infected giant cells. When stained for the nuclear protein, results showed substantial infection/transfection of the growing MB49 tumor as well. While infected/transfected normal mucosa also stained for the encoded antigen, there was an apparent preferential staining in the tumor itself. No signs of any local or systemic acute toxicity were observed. The ability of vaccinia virus to kill bladder tumor cells was not assessed in these experiments.

The ability of the vaccinia virus to infect tumors in vivo in systemically immune mice was also examined. Experiments were performed as before in naive animals except mice were injected intraperitoneally with native vaccinia, followed by instillation of the MB49 tumor intravesically. Two weeks later, the tumor was established and mice were treated with the recombinant vaccinia intravesically. Twelve hours later the bladders were removed and stained immunohistochemically for the recombinant nuclear protein antigen. Results showed that intravesical administration of recombinant vaccinia containing the nuclear protein gene transfects intravesically growing MB49 in the presence of systemic immunity. In addition, cytologic changes were noted including ballooning degeneration and intranuclear inclusion bodies. These data demonstrate that systemic immunity, which would be expected to occur in adult patients following initial vaccinia treatments, does not prevent intravesical tumor infection upon subsequent treatment with the virus. Again, the ability of vaccinia virus to kill bladder tumor cells was not assessed in these experiments.

In addition, patients with invasive bladder cancer (transitional cell carcinoma, TCC) have been treated intravesically with vaccinia prior to cystectomy. Following assessment of immunocompetence, four patients were vaccinated on the upper arm with wild type vaccinia virus ($10^7$ PFU). After demonstrating an anti-vaccinia response, escalating doses of vaccinia were instilled intravesically for a total of three doses with the last dose given 24 hours prior to cystectomy. The doses administered ranged from 1 to $100 \times 10^6$ PFU. Upon examination of the cystectomy specimens of the four patients, significant vaccinia-induced inflammatory infiltrates were seen in the mucosa and submucosa with doses of $100 \times 10^6$ PFU (three of the four patients were given that dose). The infiltrate consisted of lymphocytes, eosinophils, and plasma cells in both tumor and non-tumor tissue. Significant mucosal edema and vascular ectasia were seen as well. Both tumor and normal urothelial cells showed evidence of viral infection (enlarged vacuolated cells with cytoplasmic inclusions). There were no clinical or laboratory manifestations of vaccinia toxicity except mild dysuria. Thus, intravesical administration of wild-type vaccinia virus is effective at infecting bladder tumor cell in patients.

The following non-limiting examples are presented to better illustrate the claimed invention.

EXAMPLES

Example 1
Measurement of Anti-Vaccinia Humoral Response

An ELISA assay was developed to measure serum titers for anti-vaccinia antibody. Ninety-six well plates are coated with a 10 µg/ml protein extract obtained from cultures of human bladder cell lines infected for 6 hours with the Wyeth strain of vaccinia virus. Following blocking with PBS plus FCS, dilution series of patient sera pre- and post-immunization are added to the wells, incubated for two hours and the plates washed. Serum anti-vaccinia antibodies are visualized using peroxidase labeled anti-human IgG heavy and light chain second reagent and OPD substrate and shown to be virus specific by using lysates from non-infected cells as controls. Titers are read as the reciprocal serum dilution yielding 50% maximum absorbance in the assay.

Example 2
Treatment of Bladder Cancer

Patient 1 was a 57 year old white female who presented with initial hematuria. Subsequent pathology revealed grade III transitional cell carcinoma with muscle invasion. Vaccination was on Day 0. Intravesical vaccinia instillations were performed on Day 7, 10, and 14 following the vaccination. Left adrenalectomy, radical cystectomy, and ileal conduit were performed on Day 15. The doses of vaccinia instilled were 1, 5, and $10 \times 10^6$ PFUs on days 7, 10 and 14 respectively. There were no clinical or laboratory manifestations of vaccinia related toxicity. Histological examination revealed slight inflammation. No significant antibody titer was noted during the short term of the treatment. Antibody developed by one month post-cystectomy.

Patient 2 was a 36 year old white male who presented with gross hematuria and left flank pain. Subsequent pathology revealed grade II-III TCC with muscle invasion. Preoperative combination chemotherapy was administered for 2 cycles and a left percutaneous nephrostomy tube was inserted. Vaccination was performed on Day 0. Intravesical vaccinia instillation was performed on Day 4, 8 and 11 following vaccination. Radical cystoprostatectomy and orthotopic ileal neobladder were performed on Day 12. The doses of vaccinia instilled were 10, 25, and $100 \times 10^6$ PFUs on days 4, 8 and 11 respectively. There were no clinical or laboratory manifestations of vaccinia related toxicity. Significant mucosal and submucosal inflammation was seen made up of lymphocytes, eosinophils, and plasma cells in both tumor and non-tumor fields. Significant mucosal edema and vascular ectasis were seen. Both tumor and normal urothelial cells showed evidence of viral infection. No significant antibody titer was noted during the short term of the treatment. Antibody developed by 1 month post cystectomy.

Patient 3 was a 64 year old white male who presented in with gross hematuria. Subsequent work up was negative. He again presented 4 years later with the passage of clots. Subsequent pathology revealed grade II-II TCC with muscle invasion. Vaccination was on Day 0. Intravesical vaccinia instillation was on Day 4, 8 and 11. Radical prostatectomy and ileal neobladder were performed on Day 12. The doses of vaccinia instilled were 25, 100, and $100 \times 10^6$ PFUs on days 4, 8 and 11, respectively. There were no clinical or laboratory signs of vaccinia related toxicity except mild dysuria. Significant mucosal and submucosal inflammation was seen made up of lymphocytes, eosinophils, and plasma cells in both tumor and non-tumor fields. Significant mucosal edema and vascular ectasis were seen. Both tumor and normal urothelial cells showed evidence of viral infection. No significant antibody titer was noted during the short term of the treatment.

Patient 4 was a 52 year old white male who presented with gross hematuria. Subsequent pathology revealed grade III TCC with muscle invasion. Vaccination was administered on Day 0. Intravesical instillations were performed on day 4, 8 and 11 following vaccination. Cystoprostatectomy and ileal neobladder were performed on day 12. The doses of vaccinia instilled were 25, 100, and $100 \times 10^6$ PFUs on days 4, 8 and 11 respectively. There were no clinical or laboratory signs of vaccinia related toxicity except mild dysuria. Significant mucosal and submucosal inflammation was seen made up of lymphocytes, eosinophils, and plasma cells in both tumor and non-tumor fields. Significant mucosal edema and vascular ectasis were seen. Both tumor and normal urothelial cells showed evidence of viral infection. No significant antibody titer was noted during the short term of the treatment.

What is claimed is:

1. A method of treating a patient suffering from bladder cancer comprising administering to the patient a wild type vaccinia virus via intravesical administration to the bladder of the patient.

2. The method of claim 1 comprising multiple intravesical administrations of said virus to the bladder of the patient.

3. The method of claim 2 wherein said multiple intravesical administrations comprise escalating doses of wild type vaccinia virus.

4. The method of claim 3 wherein the patient is first vaccinated with wild type vaccinia virus prior to said intravesical administration of wild type vaccinia virus.

5. The method of claim 4 wherein said vaccination comprises intradermal administration wild type vaccinia virus.

6. The method of claim 1 wherein the bladder cancer is superficial bladder cancer.

7. The method of claim 6 wherein the bladder cancer is BCG-refractory superficial bladder cancer.

* * * * *